US006228112B1

United States Patent
Klootz et al.

(10) Patent No.: US 6,228,112 B1
(45) Date of Patent: May 8, 2001

(54) ARTIFICIAL HEART VALVE WITHOUT A HINGE

(76) Inventors: Jack Klootz, 82 Erin Way, Naples, FL (US) 34109; Brian W. Hummel, 826 Cal Cove Dr., Ft. Myers, FL (US) 33919

( * ) Notice: Subject to any disclaimer, the term of this patent is extended or adjusted under 35 U.S.C. 154(b) by 0 days.

(21) Appl. No.: 09/312,686

(22) Filed: May 14, 1999

(51) Int. Cl.[7] .................................................. A61F 2/24
(52) U.S. Cl. .......................................... 623/2.25; 623/2.23
(58) Field of Search .......................... 623/2.1, 2.2, 2.21, 623/2.22, 2.23, 2.24, 2.25, 2.26, 2.27, 2.28, 2.32, 2.34

(56) References Cited

U.S. PATENT DOCUMENTS

| | | | | |
|---|---|---|---|---|
| Re. 30,507 | * | 2/1981 | Kaster ................................. | 623/2.24 |
| 4,159,543 | * | 7/1979 | Carpentier ................................ | 3/1.5 |
| 4,225,980 | * | 10/1980 | Ramos-Martinez ...................... | 3/1.5 |
| 4,306,319 | * | 12/1981 | Kaster ...................................... | 3/1.5 |
| 4,425,670 | * | 1/1984 | Figuera .................................... | 3/1.5 |
| 4,655,772 | * | 4/1987 | De Liotta et al. ....................... | 623/2 |
| 4,822,355 | * | 4/1989 | Bhuvaneshwar ......................... | 623/2 |
| 4,957,503 | * | 9/1990 | Bukatov et al. .......................... | 623/2 |
| 5,135,538 | * | 8/1992 | Pawlak et al. ............................ | 623/2 |

* cited by examiner

*Primary Examiner*—David H. Willse
*Assistant Examiner*—Alvin Stewart
(74) *Attorney, Agent, or Firm*—Malin Haley & DiMaggio, P.A.

(57) ABSTRACT

A prosthesis for use in a human heart as a valve that reduces or eliminates blood stagnation, and therefore, the possibility of thrombosis while increasing available blood flow area through the artificial heart valve without using hinges which can become inoperable due to interaction with blood and human tissue. The artificial heart valve includes a supporting ring, a pair of radially-disposed supporting arms having specially designed and support heads of a particular shape and a pair of semi-circular valve plates that hang from the support arm and engage the support arm heads. The valve plates each include a specially designed slot that receives the support arm head which allows movement of each of the valve plates during operation of the valve to prevent accumulation of human tissue from blocking the operation of the valve. Also, the support ring aperture, in conjunction with the support ring and the mounting of the valve plates has a configuration that aids in blood flow through the valve thereby preventing stagnation and the possibility of thrombosis.

2 Claims, 4 Drawing Sheets

ARTIFICIAL HEART VALVE WITHOUT A HINGE

CROSS-REFERENCE TO RELATED APPLICATIONS

N/A

STATEMENT REGARDING FEDERALLY SPONSORED RESEARCH OR DEVELOPMENT

N/A

BACKGROUND OF THE INVENTION

1. Field of the Invention

This invention relates to a prosthesis for use in a human heart as a valve and specifically to an artificial heart valve that reduces or eliminates stagnation and the possibility of thrombosis while increasing the available blood flow area through the valve without using hinges.

2. Description of Related Art

The use of artificial prostheses as substitutes for valves in the human heart is known in the prior art. The human heart has four one-way valves which, based on the hemostatic pressure on either side of the valve, allows blood to flow through the valve in one direction while preventing the flow of blood in the opposite direction. There is a valve between the right atrium and the right ventricle and a valve between the right ventricle and the pulmonary artery which goes to the lungs. There is a valve from the left atrium to the left ventricle and a valve between the left ventricle to the aorta. Although the use of artificial heart valves have been quite successful to replace defective human heart valves, there are some drawbacks that are of concern. Specifically, if the cross-sectional structure and configuration of the artificial valve, when open, is such that local areas of the valve structure itself impede blood flow through the valve opening, the result is blood flow stagnation at the same time the blood is being pumped through the valve opening. Stagnation is a term that means a lack of blood flow or blood movement caused by obstructions in the flow path. Such stagnation in the blood flow can possibly cause thrombosis, which is undesirable.

Another problem with many artificial heart valves is that the valve mechanisms typically include hinges which can become immobile through interaction with organic material in the blood stream and the surrounding blood vessels which can cause the valve mechanism itself to malfunction. A hinged heart valve usually includes one or two barrier plates that are connected by one or more hinges to an annular frame. The plates open or close based on hemostatic pressure on each side of the heart valve, pivoting about the hinge mechanism. If the hinge fails, the plates are stuck open, closed or partially open resulting in a dangerous medical problem. It is desirous to eliminate hinge problems in artificial heart valves.

U.S. Pat. No. 4,183,103 issued to Bloch, Jan. 15, 1980, shows a prosthetic one-way heart valve that uses a circular disc. The circular disc is supported in such a way that it occupies the center of the chamber thus blocking a significant amount of blood flow when the valve is open. U.S. Pat. No. 4,416,029 issued to Kaster, Nov. 22, 1983 shows a tri-leaflet prosthetic heart valve that uses three leaflets suspended on a plurality of arms which also act to increase the complexity of the device while at the same time blocking significant portions of blood flow through the valve opening. U.S. Pat. No. 4,494,253 issued to Bicer, Jan. 22, 1985 shows a cardiovascular valve prosthesis using a circular disc that is mounted in the open position near the center of the valve, blocking blood flow.

U.S. Pat. No. 4,532,659 shows a prosthetic heart valve with a plano-convex disc occluder. In the valve open position, the disc shaped surface occupies a center portion of flow through the valve. U.S. Pat. No. 4,655,772 shows a cardiac valvular prosthesis issued to Dr. Liotta et al, Apr. 7, 1987. This artificial heart valve shows a pair of leaflets which are hinged to permit movement of the leaflets from the closed to the open position. The hinge structure and action are undesirable and include hinge stops which protrude into the mainstream of the blood flow in an open position resulting in areas of potential stagnation and hinge problems because of the hinge structure. U.S. Pat. No. 4,713,071 issued Dec. 15, 1987 to Iofis, et al, shows a heart valve prosthesis with a disc that is slightly offset but that still occupies a large flow area near the center of flow thereby reducing flow.

U.S. Pat. No. 4,822,355 issued Apr. 18, 1989 shows a heart valve assembly that again has a disc mounted in the open position to occupy a central portion of the valve, blocking flow. U.S. Pat. No. 5,135,538 issued Aug. 4, 1992 to Pawlek, et al shows a disc shaped valve member that is slightly offset from the center of flow.

Thus the prior art shows artificial heart valves which by their construction and design impede blood flow when the valve is in an open position which can create stagnation leading to thrombosis and which include hinges in some instances that themselves can be subject to malfunction due to interaction with organic materials in the bloodstream and the vessel network.

The present invention overcomes the problems shown in the prior art.

BRIEF SUMMARY OF THE INVENTION

A cardiac valvular prosthesis comprising a support ring having an aperture therethrough attachable to human heart tissue, a first and second semi-circular blood impervious valve plates sized for mounting within the support ring aperture, each valve plate having a diametral straight edge that is angularly beveled, a first and second rigid narrow valve plate support arms, radially and diametrically disposed within the support ring, the first and second support arms having a teardrop-shaped support head at one end, for movably supporting the first and second valve plates respectively, the first and second valve plates having specially shaped slots disposed at the center of gravity of each valve plate sized to receive the support arm support head, each of the valve plate slots having an elongated portion to permit movement of each valve plate perpendicular to the diametral edge and sufficiently narrow in relation to the support head to prevent valve plate movement in the diametral direction such that the valve plates close the valve and stop blood flow in one direction through the valve based on hemostatic pressure and the valve plates become parallel to allow blood flow through the valve in the opposite direction.

The cardiac valvular prosthesis also includes means connected to the support ring to resist the first and second valve plates removal from the valve during operation.

Specifically, the cardiovascular valvular prosthesis provides a one-way valve for use in a human heart comprising an annular support ring made of a suitable material for attachment to human tissue when implanted in a human heart, a pair of semicircular, rigid, flat thin valve plates sized for mounting within said support ring, each of said valve plates having a proximal side and a distal side indicating the direction of the flow of blood, each of said valve plates having a strategically sized and shaped recessed groove on the distal side near the center of gravity of each valve plate.

The annular support ring includes two radially-oriented, diametrically-opposed, rigid, narrow support arms, each of which terminates in a teardrop shaped head that contacts one valve plate on the distal side, supporting and retaining each valve plate within the support ring body.

The support ring also includes four valve plate stops, two stops for each disk to align each disk in the valve open positions. The valve plate stops are shaped to minimize fluid drag as the blood flows through the support ring center opening and the valve plates are centrally parallel to the blood flow in the valve open position.

The one-way valves open and close in response to a hemostatic pressure differential on each side of the valves. Higher pressure on the distal side of each disk opens the valve allowing blood to flow through, the valve plates being substantially parallel in the open position. Higher blood pressure on the proximal sides of the valve plates results in the valve plates contacting each other along their beveled edges blocking blood flow into the valve. The bottom edges of the valve plates are beveled and when closed, form a closure thereby impeding blood flow.

Each valve plate is movably mounted within the annular support ring on the teardrop shaped head of the support arm which contacts the central recessed groove in each distal side of each valve plate. The valve plate's distal side recess is sized in length to permit some movement of the valve plate between an open position and a closed position. The valve plates move by the hemostatic pressure on either side of the valve. As stated before, the heart valve is a one-way valve which permits flow in one direction but prevents flow in the opposite direction. This is accomplished by having the pair of semi-circular valve plates contact each other in the closed position preventing blood from flowing through the annular support body in one direction, while being parallel to each other in the open position when the blood flow is through the heart valve opening. There is minimal turbulent flow when the valve opens due to the unique bi-leaflet design of the valve.

Note that using two semicircular valve plates that are mounted, one on each side of the support ring body, allows for a significant central flow area on both sides of the valve plates, preventing or eliminating stagnation and therefore the chance of thrombosis.

The shape of each valve plate support arm on each side of the support-ring is such that when the heart valve is in the open position with the valve plates parallel to the flow of blood, perpendicular to the support ring body and parallel to each other, each valve plate is securely supported by the support arm and cannot become dislodged. In the closed position, the valve plates are touching along their diametral straight edges and engage each other, preventing blood from flowing in the opposite direction through the annular support ring. The valve plates are also prevented from being disconnected from the support arm on each side by the two pairs of valve plate stops which protrude slightly into the valve opening defining the support ring inner area.

The material selected for the annular support ring, the support arm and head, the valve plates and the valve plate stops, would be those that are the most beneficial to the patient and have the least deleterious effect on the health of the patient.

The recessed portions on the valve plate distal sides which contact the support arm heads are strategically shaped (preferably as a truncated trapezoid) so that each valve plate as it is supported on the support arm head is free to have some play or movement allowing the valve plate to freely move between the valve open and closed positions avoiding a fixed hinge action. This also permits more valve plate movement in allowing the valve plate to move to a 90° position relative to the annular circular valve opening in the open position.

It is an object of this invention to provide an improved cardiovascular, valvular prosthesis.

It is another object of this invention to provide an improved artificial heart valve that reduces or eliminates stagnation in the blood flow thereby reducing the possibility of thrombosis.

And yet another object of this invention is to provide an artificial heart valve that operates without hinges.

In accordance with these and other objects which will become apparent hereinafter, the instant invention will now be described with particular reference to the accompanying drawings.

DETAILED DESCRIPTION OF THE INVENTION

Figure 1:
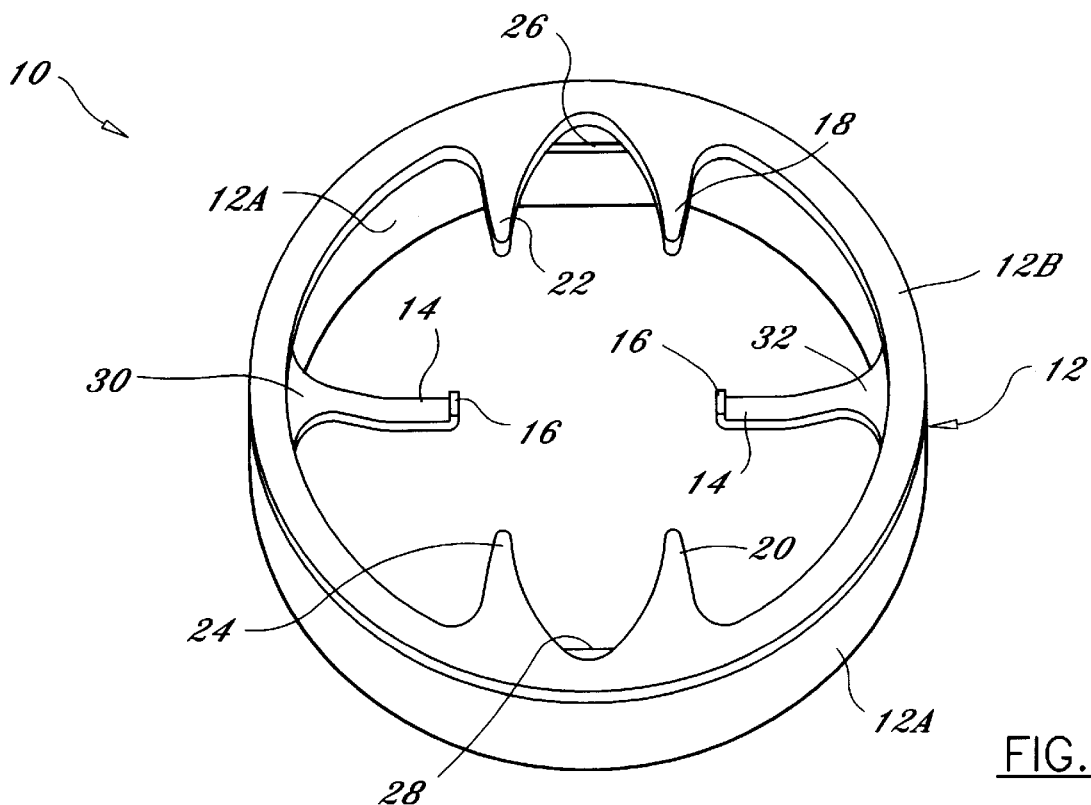
FIG. 1 shows a top perspective view of the invention without the barrier valve plates.

Referring now to FIG. 1, the artificial heart valve annular support ring is shown at 10 and includes a rigid body 12 that includes a rigid cylindrical ring 12a having an outer wall area that is attached to the patient's heart tissue by conventional fastening techniques. The rigid annular support body 10 can be manufactured of any bio-compatible material that is known in the art, such as titanium. The titanium ring can be encircled by a woven Dacron material enabling a surgeon to pass suture material to attach the valve to heart structures.

Unitarily formed as part of the annular support body 12 are a pair of diametrically opposed support arms 14 terminating at their free ends in a predetermined teardrop shaped head 16. Each support arm 14 is attached or unitarily formed as part of the annular support body 12 through support arm base 30 and 32. Support arms 14 are connected to the annular support body by bases 30 and 32, which are essentially diametrically opposed from each other, 180° apart.

The purpose of each support arm 14 and the support arm 16 is to support and retain a semicircular valve barrier valve plate, one semi-circular valve plate on each side. Each valve plate serves as a liquid barrier when the valve is closed to prevent blood flow through the valve. A specially configured surface plate 12b permanently affixed to support ring 12a forms the top of the valve body.

The top surface plate 12b in FIG. 1 includes two valve plate stops 22 and 24 on one side of the support body 12 and two valve plate stops 18 and 20 on the opposite side of the support body 12.

Figure 2:
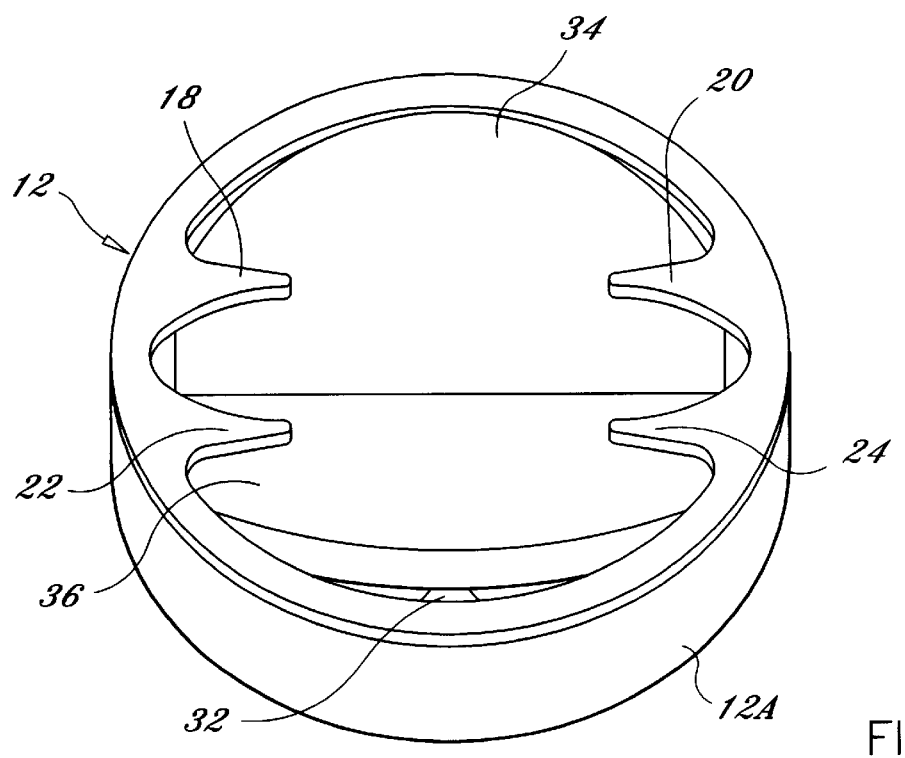
FIG. 2 shows a top perspective view of the invention with the valve plates in place representing the closed position of the valve.
Figure 3:
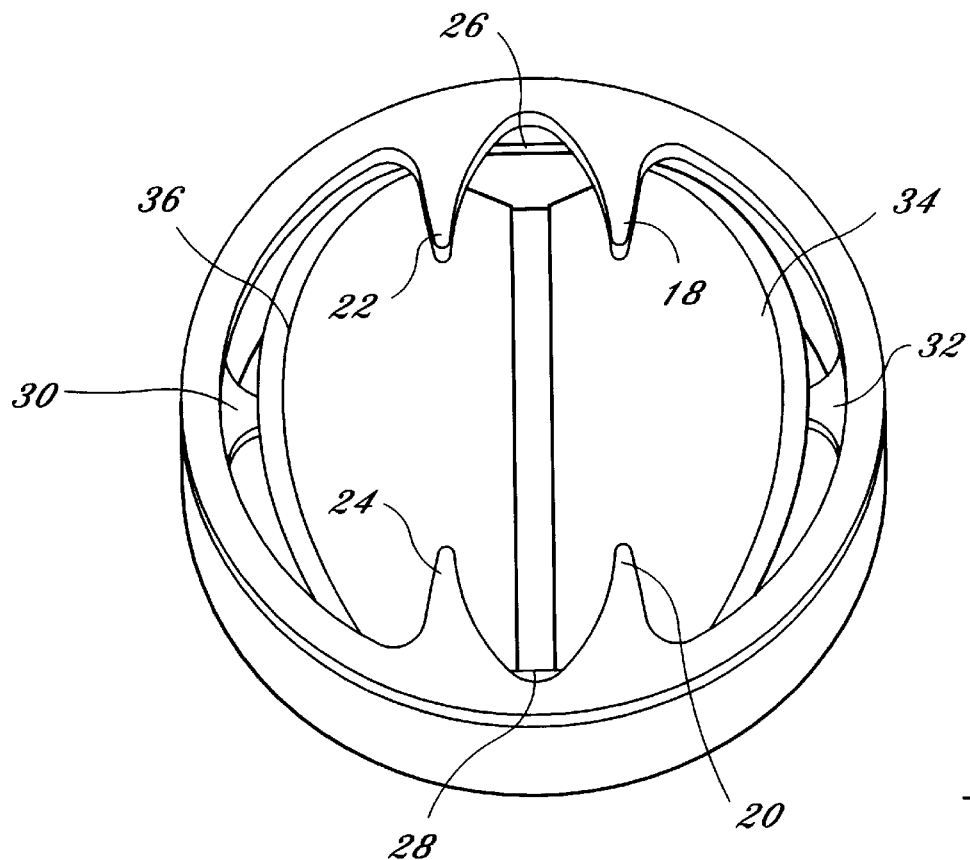
FIG. 3 shows the valve of FIG. 2 rotated 90 degrees.

As shown in FIGS. 2 and 3, semicircular blood barrier valve plates 34 and 36 act as fluid barriers when the valve plate bottom beveled edges are in contact as a one-way valve to prevent blood flow through the valve in a first direction. The valve plates 34 and 36 can be made from a suitable material such as pyrolytic carbon. The valve plates move about the support arms 14 due to the hemostatic pressure differences on each side of the valve 10 which causes the blood to flow through the valve 10 moving the valve plates into a parallel disposition, allowing for maximum blood flow through the middle of the valve and on both sides of each valve plate. This can best be seen in FIG. 7. The valve plates 34 and 36 are movably supported on the support arms 14. Specifically, each support arm head 16 engages a strategically-sized, recessed slot located in the approximate geometrical center of gravity of each valve plate that allows for some movement of each valve plate back and forth relative to head 16. Note that the support head 16 is not hinged with the barrier valve plate. Each valve plate support slot contacts the support arm head 16 that restrains the valve plate from side-to-side but allows the valve plate to have a certain amount of up and down movement when the valve transitions from the closed position to the open position and from the open position to the closed position. The dimensions of the slot will vary, according to the size of the valve. Valve sizes can range from 19 mm to 27–28 mm in diameter in the aortic position and 27 mm through 35 mm in diameter in the mitral position. In the open position, the valve plate stops prevent the valve plates from flipping past center, keeping the valve plates essentially parallel to each other in the valve open position.

Figure 4:
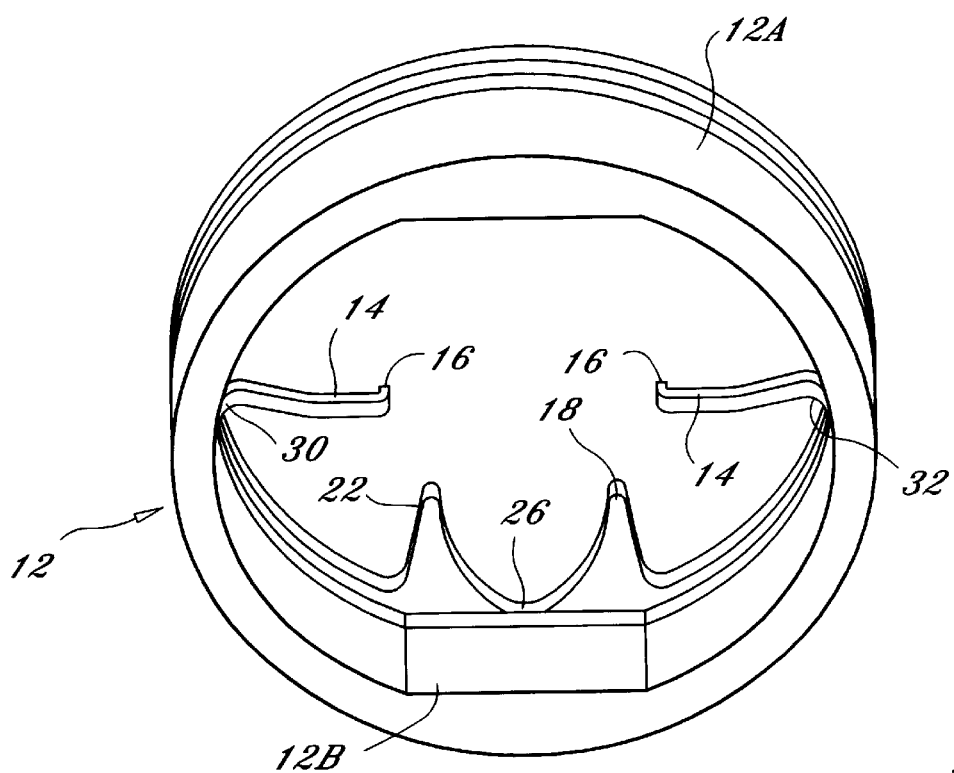
FIG. 4 shows a bottom perspective view without the valve plates.
Figure 5:
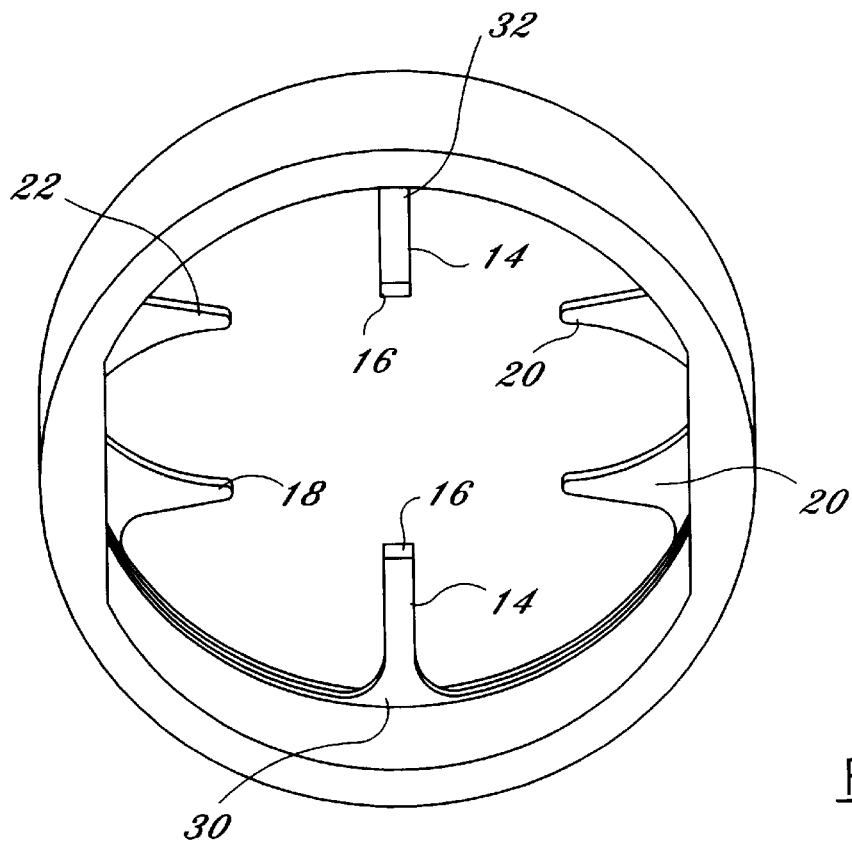
FIG. 5 shows the same view as FIG. 4 with the invention rotated 90° without the valve plates.

FIGS. 4 and 5 show the relationship between the support arms 14 within annular support body 12a. The valve plate stops 18 and 22 project into the support body 12a and are curved on one edge and substantially straight on the other edge with curved tips to reduce turbulent blood flow when the valve is open. Beneath each valve plate stop on the inside wall of the support body are flat areas which correlate to the flat side edge of each valve plate for a good fit in the closed position.

Figure 6:
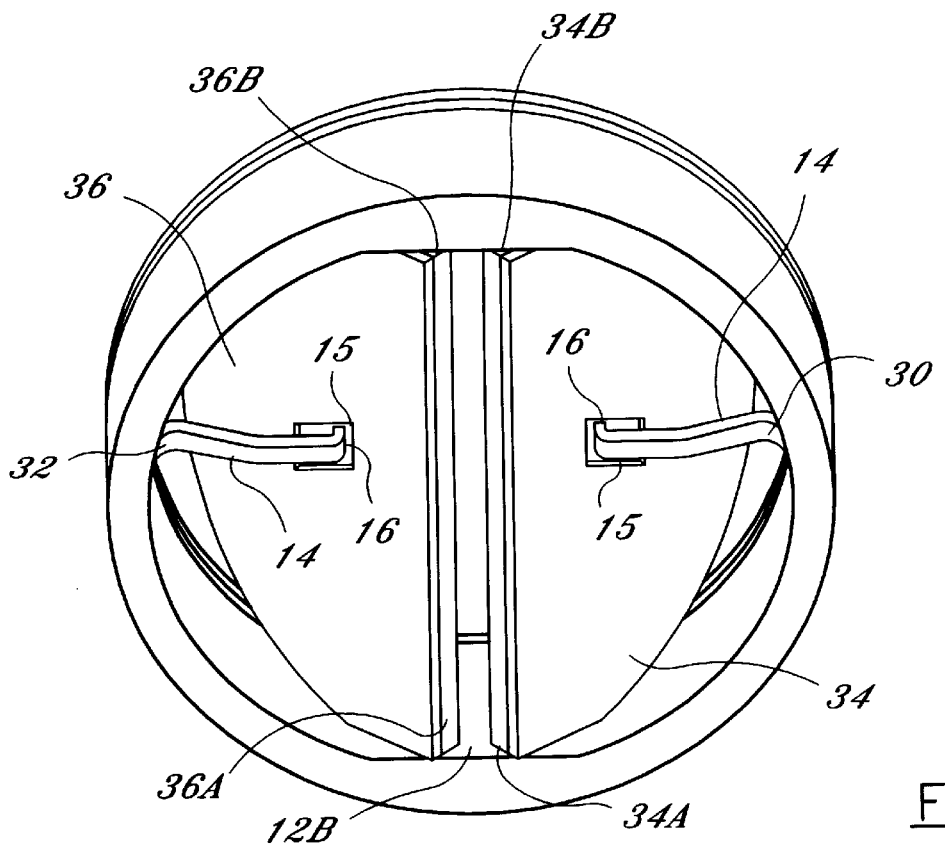
FIG. 6 shows a bottom view perspectively with the valve plates shown slightly open.
Figure 7:
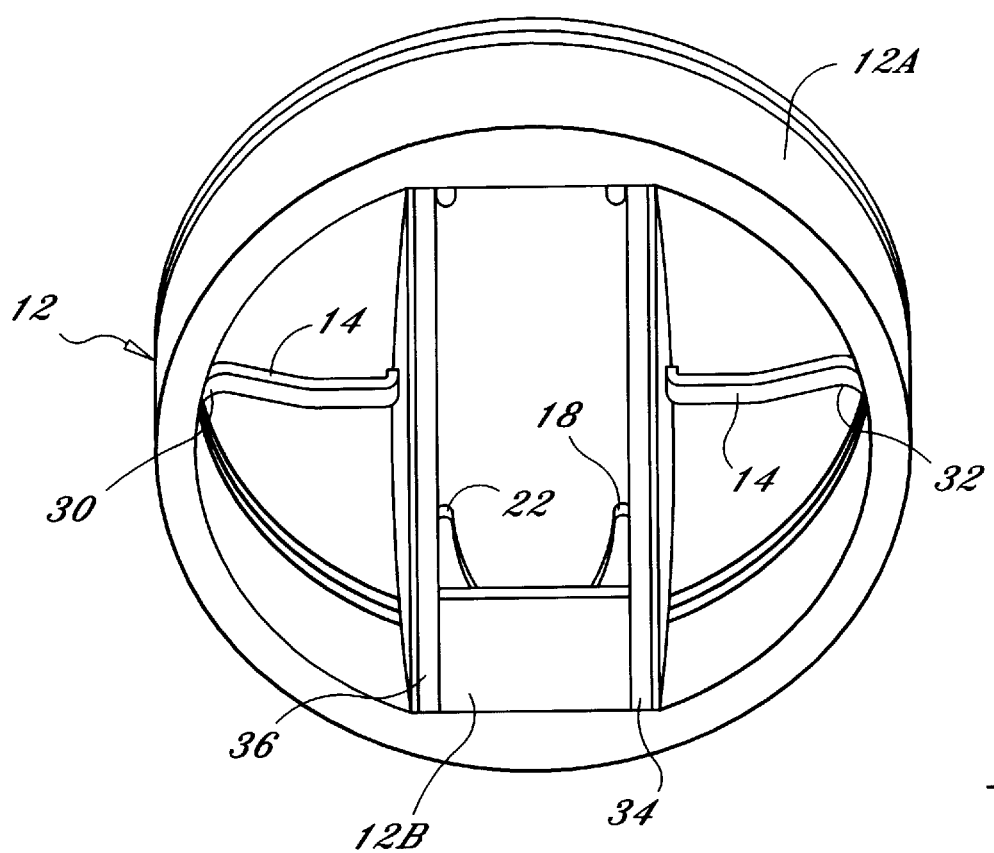
FIG. 7 shows a bottom view perspectively with the valves plates in the open position.

FIGS. 6 and 7 are shown for illustration purposes only where FIG. 6 represents the valve where the plates are slightly open, while FIG. 7 shows the valve where the plates are completely open. In a closed position the flat diametrical end faces of each valve plate would be in contact with each other preventing blood flow through the annular support body. In the completely open position, shown in FIG. 7, the valve plates 34 and 36 would be nearly parallel.

FIG. 7 shows barrier valve plates held on the support arm 14 and support flange 16 (not shown) engaged in a truncated or trapezoidal recessed slot. Movement of the valve plate prevents the accumulation of organic material in the slot. As shown in FIG. 7, the support flange 16 (seen in FIG. 5) can engage the slot of the valve plate in such a way as to movably support the valve plate on the arm 14, positioning the plates in an open, nearly parallel position.

In summary, the present invention provides a one-way artificial heart valve having essentially uninterrupted blood flow in one direction through the valve opening, around unchanged semi-circular valve plates, and in the opposite direction, preventing blood flow. This is accomplished without rotatable hinges and in such a way as to provide maximum flow around the valve plates in the open position. This greatly reduces stagnation and therefore thrombosis.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. A cardiac valvular prosthesis comprising:

a support ring having an aperture therethrough attachable to human heart tissue;

first and second semi-circular blood impervious valve plates sized for mounting within said support ring aperture, each valve plate having a diametral straight edge that is angularly beveled;

first and second rigid narrow valve plate support arms, radially and diametrically disposed within said support ring, said first and second support arms having a teardrop-shaped support head at one end, for movably supporting said first and second valve plates respectively, said first and second valve plates having specially shaped slots disposed at the center of gravity of each valve plate sized to receive said support arm support head, each of said valve plate slots having an elongated portion to permit movement of each valve plate perpendicular to the diametral edge and sufficiently narrow in relation to said support head to prevent valve plate movement in the diametral direction; such that said valve plates close said valve and stop blood flow in one direction through said valve based on hemostatic pressure and said valve plates become parallel to allow blood flow through said valve in the opposite direction.

2. The cardiac valvular prosthesis as in claim 1 including:

means connected to said support ring to resist said first and second valve plates removal from said valve during operation.

* * * * *